(12) United States Patent
Smith et al.

(10) Patent No.: US 8,979,787 B2
(45) Date of Patent: Mar. 17, 2015

(54) TREATMENT OF PRE-ECLAMPSIA USING TARGETED APHERESIS

(76) Inventors: Henry John Smith, Temecula, CA (US); James Roger Smith, Laguna Niguel, CA (US)

( * ) Notice: Subject to any disclaimer, the term of this patent is extended or adjusted under 35 U.S.C. 154(b) by 336 days.

(21) Appl. No.: 13/374,814

(22) Filed: Jan. 17, 2012

(65) Prior Publication Data
US 2012/0215150 A1    Aug. 23, 2012

Related U.S. Application Data

(60) Provisional application No. 61/461,531, filed on Jan. 20, 2011.

(51) Int. Cl.
*A61M 37/00* (2006.01)
*A61M 1/34* (2006.01)

(52) U.S. Cl.
CPC ........... *A61M 1/3472* (2013.01); *A61M 1/3486* (2014.02)
USPC ........................................ 604/5.01; 604/6.01

(58) Field of Classification Search
USPC .................. 604/4.01–6.16; 424/178.1–183.1, 424/78.31; 514/59
See application file for complete search history.

(56) References Cited

U.S. PATENT DOCUMENTS

| | | | |
|---|---|---|---|
| 6,866,846 B1 * | 3/2005 | Heinrich et al. | 424/140.1 |
| 8,449,489 B2 * | 5/2013 | Thorn et al. | 604/6.03 |
| 2009/0192434 A1 * | 7/2009 | Thorn et al. | 604/6.03 |
| 2011/0280825 A1 * | 11/2011 | Karumanchi | 424/78.31 |

* cited by examiner

*Primary Examiner* — Philip R Wiest
(74) *Attorney, Agent, or Firm* — Stetina Brunda Garred & Brucker

(57) ABSTRACT

This invention uses "targeted apheresis" to treat pregnant women who are at risk of developing eclampsia. "Targeted Apheresis" is a process whereby certain growth factor receptors (sFlt-1) circulating in the blood of a pregnant woman at risk of developing pre-eclampsia are selectively removed by passing the blood through a cartridge containing immobilized anti-sFlt-1 aptamers. The circulating sFlt-1 is bound out by the immobilized anti-sFlt-1 aptamers and the cleaned blood is returned to the patient. Removal of circulating sFlt-1 will diminish the risk of developing eclampsia during pregnancy.

7 Claims, 1 Drawing Sheet

Affinity cartridge containing anti-sFlt-1 aptamer coated beads (highly magnified)

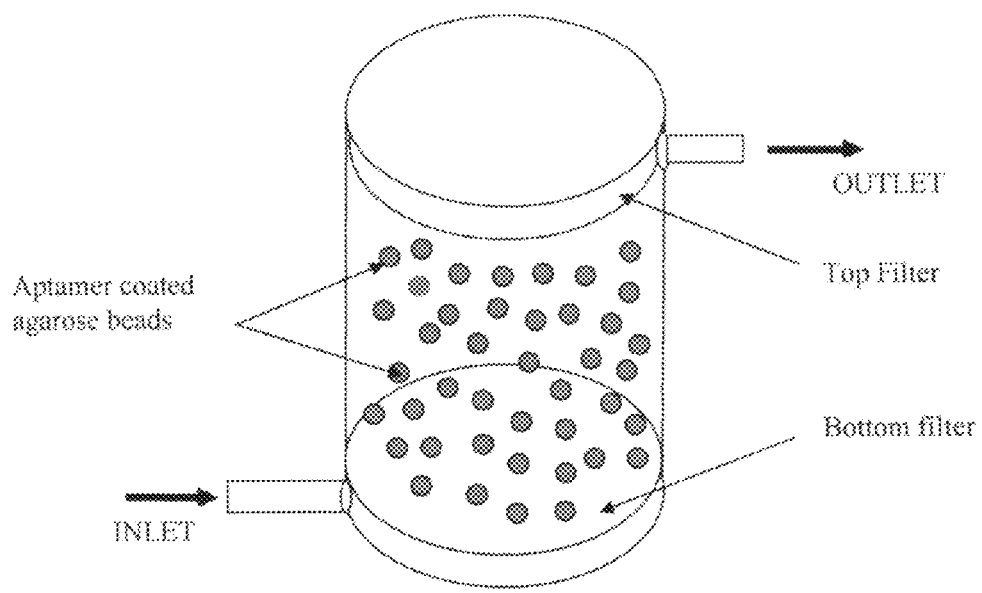
Figure 1. Affinity cartridge containing anti-sFlt-1 aptamer coated beads (highly magnified)
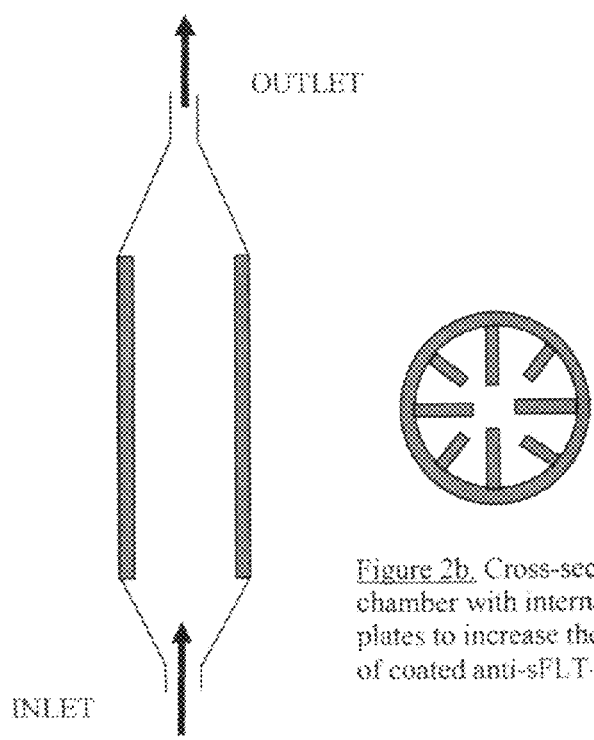
Figure 2b. Cross-section of chamber with internal projecting plates to increase the surface area of coated anti-sFLT-1 aptamers.
Figure 2a. Flow thru affinity chamber with inner walls coated with anti-sFLT-1 aptamers.

TREATMENT OF PRE-ECLAMPSIA USING TARGETED APHERESIS

CROSS-REFERENCE TO RELATED APPLICATIONS

This invention claims priority to Provisional Patent Application Ser. No. 61/461,531 filed Jan. 20, 2011 and titled: Treatment of pre-eclampsia using targeted apheresis.

STATEMENT RE: FEDERALLY SPONSORED RESEARCH/DEVELOPMENT

Not Applicable

BACKGROUND

Pre-eclampsia or toxemia during pregnancy is one of the leading causes of maternal and infant mortality. The symptoms of pre-eclampsia typically appear after the 20th week of pregnancy and are characterized by high blood pressure, edema and protein in the urine. In severe cases there is a massive rise in blood pressure that can result in severe complications, premature delivery of the baby and death of the mother or baby.

Pre-eclampsia can vary in severity from mild to life threatening. The mild form of pre-eclampsia is usually treated with bed rest and frequent monitoring. For moderate to severe cases, hospitalization is recommended and the patient is treated with blood pressure medication or anticonvulsant medications to prevent seizures. If the condition becomes life threatening to the mother or the baby the pregnancy is terminated and the baby is delivered pre-term.

Recent research has shown that the proper development of the fetus and the placenta appears to be mediated by several growth factors. One of these growth factors is placental growth factor (PlGF) and the other is vascular endothelial growth factor (VEGF). Placental growth factor (PlGF) is a VEGF family member that is capable of inducing proliferation, migration, and activation of endothelial cells. PlGF binds as a homodimer to the Flt-1 receptor found on trophoblast cells. VEGF is an endothelial cell-specific mitogen, an angiogenic inducer, and a mediator of vascular permeability. VEGF binds as a homodimer to the homologous tyrosine kinase receptors, the fms-like tyrosine kinase (Flt-1) receptor and the kinase domain receptor (KDR).

A soluble form of the Flt-1 receptor (sFlt-1) was recently identified in the blood of pregnant women. Women with pre-eclampsia had higher levels of sFlt-1 than women with normal pregnancy. The circulating sFlt-1 receptors are believed to compete with the membrane fixed cellular Flt-1 receptors and act as a "physiologic sink" to down-regulate VEGF signaling pathways by binding to circulating PlGF and VEGF. It was postulated that women who produced large amounts of sFlt-1 early in their pregnancy were prone to develop pre-eclampsia.

Researchers have suggested several different therapeutic approaches to treat pre-eclampsia. One approach is to increase the level of PlGF and/or VEGF by injecting these compounds into the patient, or by utilizing drugs that stimulate the increased production of PlGF and/or VEGF. Increasing the amount of PlGF and VEGF in the presence of large amounts of sFlt-1 however, is analogous to driving a car and stepping on the gas while the brakes are still on. It would be preferable to reduce the level of circulating sFlt-1 so that the natural PlGF and VEGF can perform their functions.

Various means of reducing the level of circulating sFlt-1 by administering pharmaceuticals and/or anti-sFlt-1 antibody to block the binding of sFlt-1 to PlGF and/or VEGF have been proposed. However, a major difficulty with using any form of drugs is that any pharmaceutical that can target sFlt-1 will also target cellular Flt-1 and cause harm to mother and baby.

It would be preferable to develop a more safe and effective process of reducing the level of circulating sFlt-1 receptors in order to allow the natural PlGF and VEGF to perform their functions.

This invention teaches a novel method of treating pre-eclampsia by reducing the level of circulating sFlt-1 using "targeted apheresis." The targeted apheresis process teaches a means of removing sFlt-1 using anti-sFlt-1 aptamers contained within an affinity device. It's important to note that the immobilized anti-sFlt-1 aptamers described herein are capable of binding to epitopes present on both sFlt-1 and cellular Flt-1. However, by using targeted apheresis only the circulating sFlt-1 receptors are selectively removed from the blood. The cellular Flt-1 receptors present on trophoblast cells cannot come into contact with the immobilized aptamers within the apheresis cartridge and therefore are unaffected by the apheresis process.

BRIEF SUMMARY

The main application of this invention is in the treatment of pregnant women who are at risk of developing eclampsia using a process of "targeted apheresis." "Targeted Apheresis" is a process whereby only the sFlt-1 receptors responsible for causing the disease symptoms are selectively removed from the blood by passing the blood or the plasma fraction through a cartridge containing immobilized anti-sFlt-1 aptamers. The sFlt-1 receptors are bound out by the immobilized anti-sFlt-1 aptamers and the cleaned blood is then returned to the patient. Removal of circulating sFlt-1 receptors will diminish the risk of developing eclampsia during pregnancy.

BRIEF DESCRIPTION OF THE DRAWINGS

These and other features and advantages of the various embodiments disclosed herein will be better understood with respect to the following description and drawings, in which like numbers refer to like parts throughout, and in which:

FIG. 1 is a perspective view of an affinity cartridge containing anti-sFlt-1 aptamer coated beads with the cartridge having inlet and outlet ports, as constructed in accordance with a preferred embodiment of the present invention.

FIG. 2a is a side cross-sectional view of a flow-through affinity chamber with inner walls coated with anti-sFlt-1 aptamers, as constructed in accordance with a preferred embodiment of the present invention.

FIG. 2b is a top cross-sectional view of a flow-through affinity chamber as illustrated in FIG. 2a with internal projecting plates to increase the surface area of coated anti-sFlt-1 aptamers.

DETAILED DESCRIPTION

This invention teaches a method of targeted apheresis for treating pre-eclampsia during pregnancy. Targeted apheresis is used to remove the circulating sFlt-1 receptors that are believed to be responsible for the symptoms of eclampsia. The inventors had earlier proposed an apheresis method for removing sFlt-1 using immobilized anti-Flt-1 antibody within an affinity device. There is however some concern regarding the use of anti-sFlt-1 antibody prepared from immunized animals because of the possibility that even a small amount of foreign protein leaching out of the immunosorbent and entering the blood may elicit an immune reaction in the patient. The inventors then made the surprising discovery that using anti-sFlt-1 aptamers instead of anti-sFlt-1 antibody in the affinity device would eliminate the possibility of causing an immune reaction in the patient; and in addition would result in many other advantages that were not previously recognized. There are no prior reports on the use of anti-sFlt-1 aptamers being used in therapeutic apheresis to treat pre-eclampsia.

Typically, pregnant women who exhibit laboratory findings and clinical signs of developing pre-eclampsia are candidates for targeted apheresis. Treatment will consist of one or more targeted apheresis treatments performed during the risk period of the pregnancy. This will typically begin about the 20th week of pregnancy and continue on a periodic basis until delivery.

Targeted Apheresis Using Anti-Flt-1 Aptamers.

Preparation of the Anti-Flt-1 Aptamer Apheresis Cartridge.

Aptamers are small (i.e. 40 to 100 bases), synthetic oligonucleotides. They may be composed as a single-stranded DNA chain (ssDNA) or a single-stranded RNA chain (ssRNA). Each aptamer has a unique configuration as a result of the composition of the nucleotide bases in the chain causing the molecule to fold in a particular manner. Because of their folded structure each aptamer will bind selectively to a particular ligand in a manner analogous to an antibody binding to its antigen. Aptamers are able to specifically recognize and bind to virtually any kind of target, including ions, whole cells, drugs, toxins, low-molecular-weight ligands, peptides, and proteins.

In order to improve bioavailability against nucleases found in vivo the oligonucleotides comprising the aptamer may be modified to avoid nuclease attack. They may for example be synthesized as L-nucleotides instead of the natural D-nucleotides and thus avoid degradation from the natural nucleases present in blood.

Aptamers are usually synthesized from combinatorial oligonucleotide libraries using in vitro selection methods such as the Systematic Evolution of Ligands by Exponential Enrichment (SELEX). This is a technique used for isolating functional synthetic nucleic acids by the in vitro screening of large, random libraries of oligonucleotides using an iterative process of adsorption, recovery, and amplification of the oligonucleotide sequences. The iterative process is carried out under increasingly stringent conditions to achieve an aptamer of high affinity for a particular target ligand such as for example sFlt-1.

Since the SELEX was first introduced there are other methods and variations of producing aptamers known to those of skill in the art. These are considered to be within the scope of this invention.

The anti-sFlt-1 aptamers (either ssDNA and/or ssRNA) are immobilized by chemically coupling them to an insoluble support matrix such as cross-linked CNBr-activated or NHS-activated agarose beads, or cellulose, or other similar material. For example, a 3'-amino modified group (3'-end-cap) is introduced that will allow coupling of the aptamer to N-hydroxysuccimide activated cross-linked agarose beads. Any remaining unbound aptamers are removed by washing the beads with a suitable solution such as buffered saline and the aptamer conjugated beads are then placed within a cartridge device. The methods of coupling aptamers to various insoluble support matrixes are known to those of skill in the art and are within the scope of this invention.

Typically, the apheresis device will be constructed as a cylinder with an inlet to allow plasma to enter at one end, and an outlet at the opposite end to allow the cleaned plasma to exit and be returned to the patient, as shown in FIG. 1. Other device configurations may also be designed and are within the scope of this invention. The cartridge device is constructed of material that is nontoxic and which provides rigid support. The material will be of a plastic composition such as polystyrene, or polyvinyl, or polypropylene or other similar material. There is an inside filter at the bottom of the device to prevent the immobilized aptamer beads from leaving the device. There is also an inside filter at the top of the device to contain the immobilized aptamer beads within the device. Typically these filters are composed of plastic and/or cellulosic material and have pores that will allow thru passage of fluid such as blood or plasma, but not large particles such as agarose beads (also shown in FIG. 1). The manufacture of these types of devices and the materials used are known to those skilled in the art and are within the scope of this invention.

Apheresis Procedure Using Immobilized Anti-Sflt-1 Aptamers.

Targeted apheresis differs from conventional apheresis in that in targeted apheresis only the pathological elements responsible for the disease or disease symptoms are removed.

The overall procedure for targeted apheresis is the same as that used in conventional apheresis. Briefly, blood from the patient is circulated extra corporeally using standard apheresis equipment. The blood is separated into the cellular elements (red blood cells, white blood cells and platelets) and fluid (plasma) elements using differential centrifugation or a membrane filter. The plasma is then circulated through the targeted apheresis device where the immobilized anti-sFlt-1 aptamers will bind to the circulating sFlt-1 receptors and remove them from circulation. The cleaned plasma is then mixed with the cellular blood elements and returned to the patient.

In one embodiment of this invention the apheresis device is composed of a tube or container in which the anti-sFlt-1 aptamers are immobilized on the inside walls of the tube or container, an exemplary illustration being shown in FIG. 2a. Blood passing thru the tube or container will come into contact with the immobilized aptamers lining the inner walls, and the circulating sFlt-1 will be bound out. The tube or container will typically be composed of a plastic composition such as polystyrene, or polyvinyl, or polypropylene or other similar material capable of being chemically modified so that the aptamers can be chemically linked to their surface. In order to increase the amount of aptamers that can be immobilized inside the apheresis device there are various ways of increasing the surface area of the interior walls of the device. For example, the tube configuration can be elongated and made into a compact coil; or the container configuration can have radial "fins" inside to increase the internal surface area (FIG. 2b). These and other design variations are considered to be within the scope of this invention. Also the materials and manufacturing methods of making these kinds of devices are known to those of skill in the art and are also considered to be within the scope of this invention.

The targeted apheresis cartridge may be employed as a single use device or it may be regenerated and used multiple times. To regenerate the device an elution buffer solution is passed through the device to release the sFlt-1 bound to the immobilized aptamers. The released sFlt-1 is then washed out of the device and the regenerated aptamer device is stored in a preserving buffer solution. Typically, the apheresis device is stored in the cold at 2-80 C

DISCUSSION

It is generally believed that an elevated level of sFlt-1 present at an early inappropriate time during pregnancy can cause pre-eclampsia. It is hoped therefore that a reduction of sFlt-1 will ameliorate the symptoms of the disease.

There are however, no current pharmaceuticals available to treat pre-eclampsia. Any pharmaceutical that has the capacity to affect the production or reduction of sFlt-1 levels also has the potential to affect cellular Flt-1 and thereby pose a significant risk of harm to mother and baby.

This invention describes an alternative approach to treating pre-eclampsia using targeted apheresis. In targeted apheresis immobilized anti-sFlt-1 aptamers are used to remove circulating sFlt-1 thus allowing the natural PlGF and VEGF to perform their functions. The advantage of targeted apheresis is that only the pathogenic sFlt-1 is irreversibly removed without affecting the normal physiological functions of PlGF or VEGF on their cellular growth receptors.

There are many advantages to using anti-sFlt-1 aptamers as the binding agent to remove sFlt-1. First, the anti-sFlt-1 aptamers are non-immunogenic and cannot elicit an allergic reaction in the patient. Second, the anti-sFlt-1 aptamers are synthesized and therefore there is no variation in their composition or reactivity. Third, the anti-sFlt-1 aptamers are synthesized and therefore there is no concern regarding biological contamination during their production. Fourth, the anti-sFlt-1 aptamers can be produced to have high selectivity and affinity for their target compounds. Fifth, the manufacturing process for anti-sFlt-1 aptamers can be standardized so there is no variation between different production batches even when they are made over a prolonged period of time. Sixth, the anti-sFlt-1 aptamers are more stable and resistant to degradation than biological materials, and therefore the apheresis devices can be stored for a prolonged period of time without losing activity. And seventh, the anti-sFlt-1 aptamers are more chemically stable than biological material and therefore after each use they can be regenerated by eluting off the bound sFlt-1 and reused.

Since the discovery of sFlt-1 and the physiological role it plays, other soluble receptors have been discovered. It is very likely that these too will be found to play a physiological role in health and disease. In those circumstances where they have a pathological effect their removal using targeted apheresis in a manner similar to that described here may provide an effective means of treatment.

This invention teaches the use of targeted apheresis to treat pre-eclampsia. The examples given here are for illustration and not as limitation. Those of skill in the art will recognize from the description and examples given in this invention other embodiments and applications that fall within the spirit and scope of this invention.

What is claimed is:

1. A method for treating pre-eclampsia in a pregnant women using targeted apheresis, the method comprising the steps of:
   a) providing an apheresis device containing immobilized anti-sFlt-1 aptamers; and
   b) passing the pregnant woman's blood through the apheresis device to selectively remove circulating sFlt-1 passing through the apheresis device.

2. The method of claim 1 wherein the anti-sFlt-1 aptamers comprise ssDNA and/or ssRNA oligonucleotides.

3. The method of claim 1 whereby wherein the apheresis device comprises an affinity cartridge containing anti-sFlt-1 aptamers conjugated to support matrix selected from the group consisting of: a cross-linked agarose support matrix; cellulose support matrix.

4. The method of claim 1 wherein the apheresis device comprises a flow-thru chamber having inner walls, the inner walls being coated with anti-sFlt-1 aptamers.

5. The method of claim 1 wherein the apheresis device is a disposable apheresis device for single use only.

6. The method of claim 1 wherein the apheresis device is a reusable apheresis device.

7. An apheresis device for the treatment of pre-eclampsia in pregnant women using targeting apheresis, the apheresis device comprising:
   an affinity cartridge having an inlet and an outlet;
   an insoluble support matrix contained within the affinity cartridge; and
   a plurality of anti-sFlt-1 aptamers chemically coupled to the insoluble support matrix.

\* \* \* \* \*